United States Patent [19]

Roubicek et al.

[11] Patent Number: 4,657,677

[45] Date of Patent: Apr. 14, 1987

[54] EQUIPMENT FOR ENHANCED MASS TRANSFER AND IN CHEMICAL AND BIOCHEMICAL PROCESSES

[76] Inventors: Rudolf V. Roubicek, 1304 Delano, Las Cruces, N. Mex. 88001; Vaclav Feres, Haid und Neu-Strasse 14, 7500 Karlsruhe 1, Fed. Rep. of Germany

[21] Appl. No.: 702,333

[22] Filed: Feb. 15, 1985

[51] Int. Cl.$^4$ .............................................. B01D 00/00
[52] U.S. Cl. ...................................... 210/219; 261/89
[58] Field of Search ................. 210/219; 261/84, 89, 261/90, 93

[56] References Cited

U.S. PATENT DOCUMENTS

| | | | |
|---|---|---|---|
| 3,779,531 | 12/1973 | White et al. | 210/219 X |
| 3,827,679 | 8/1974 | Kaelin | 210/219 X |
| 3,965,009 | 6/1976 | Kaelin | 210/219 X |
| 3,980,740 | 9/1976 | Bos | 210/219 X |
| 4,117,047 | 9/1978 | Hannecart | 210/219 X |
| 4,153,500 | 5/1979 | Feres | 159/6 R |
| 4,167,454 | 9/1979 | Feres | 202/236 |
| 4,193,949 | 3/1980 | Naito | 210/219 X |
| 4,339,398 | 7/1982 | Feres | 261/89 |

Primary Examiner—Tom Wyse
Attorney, Agent, or Firm—Milton D. Wyrick

[57] ABSTRACT

A device based on rotating surfaces for promoting highly efficient molecular diffusive transfer between gases and liquids is described. Said transfer is achieved by generating a thin film of liquid which flows on a rotating surface, thereby exposing a large area of flowing liquid to the gaseous phase. This device is especially useful in promoting efficient molecular transfer of gases with low solubility in the liquid, e.g., oxygen into an aqueous phase in conventional aerobic fermentation vessels. The principle of this system can be employed in the reverse direction of transfer, for gases leaving the liquid phase, such as occurs in stripping, defoaming and deodorization. Of special value is the prevention of forming, a common problem in the operation of conventional fermentation processes which occurs as the molecular transfer takes place.

16 Claims, 11 Drawing Figures

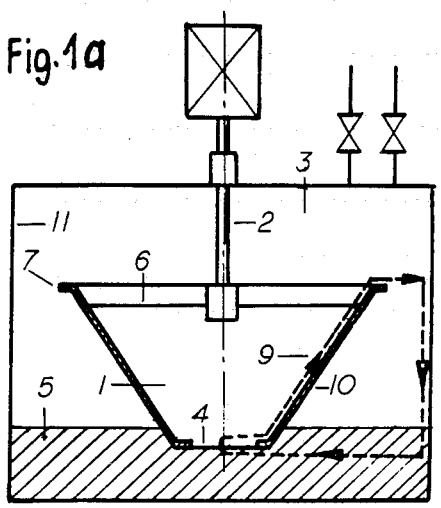
Fig. 1a
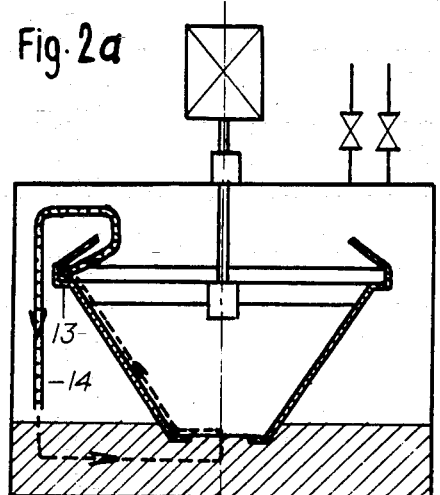
Fig. 2a
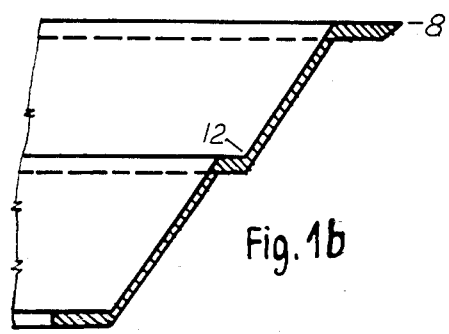
Fig. 1b
Fig. 2b
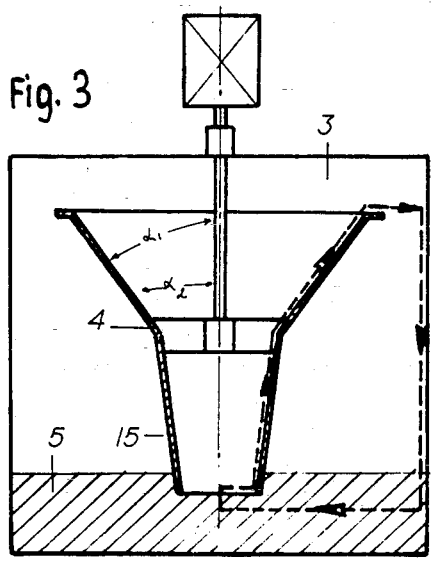
Fig. 3
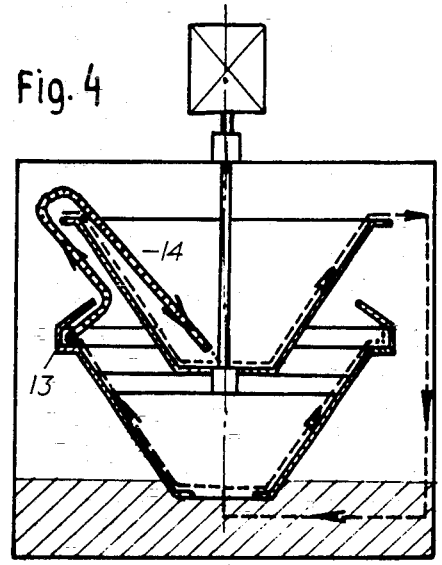
Fig. 4

DISSOLVED OXYGEN VS TIME FOR DIFFERENT MIXING SCHEMES

LEGEND:

P   Power

1   Cone rotating at 150 rpm.
2   Open turbine rotating at 150 rpm. No air fed into vessel.
3   Open turbine rotating at 150 rpm. Air fed at 1 liter/min.
4   Cone rotating at 250 rpm.
5   Cone rotating at 350 rpm.

EQUIPMENT FOR ENHANCED MASS TRANSFER AND IN CHEMICAL AND BIOCHEMICAL PROCESSES

BACKGROUND OF THE INVENTION

In aerobic biological processes the oxygen supply by aeration is of primary importance, but the low solubility of atmospheric oxygen in water, about 9 ppm at 20° C., limits its transfer. Unlike the higher plants, most microorganisms lack the structures necessary for direct absorption of oxygen from air, and thus the supply of oxygen through the cell wall of the microorganism to the enzymatic system responsible for respiration must be accomplished through an external aqueous medium. Thus, this limited reservoir of dissolved oxygen is quickly depleted by actively growing aerobic microorganisms unless it is rapidly replenished by some source, typically by molecular diffusion from air. Further, the solubility of oxygen in typical industrial nutrient medium is even lower, sometimes half that in pure water, and can act as only a very small reservoir of available oxygen. Hence, oxygen supply and the efficiency of its method of distribution are typically limiting factors for the growth of aerobic microorganisms in liquid substrates. The efficient industrial cultivation of aerobic microorganisms is dependent on solving the problem of supplying oxygen at a rate sufficient to meet the inherent demand of the particular species of microorganism being cultivated on large scale.

Conventional equipment in which microorganisms are propagated generally consists of a vessel equipped with mechanical agitation and a means for introducing gases such as oxygen, air or carbon dioxide. Molecular transport between bubbles of the gas phase and the fermentation liquor is enhanced by mechanical agitation. The work expended to enhance molecular transport in this manner ranges up to 1 horsepower per 100 gallons of fermentation liquor. Additional energy must be expended in supplying the necessary gases which are conventionally introduced at a rate up to 1 volume of gas per volume of fermentation liquor per minute through a sparging system located below the mechanical agitator. Conventional equipment for promoting high rates of oxygen transfer to the liquid phase in chemical and biological reactors promote good gas distribution throughout the liquid phase by stirring. Such stirrers use various impeller designs alone or in combination with a draft tube, suction tube, baffles and other similar flow modification devices. In special circumstances efficient gas distribution is achieved utilizing air entrainment, such as by pumping liquid or gas-liquid mixtures through a jet or aspirator. Modified air lift systems have also been employed to enhance oxygen transfer in biological and chemical processes. The high cost of mechanical energy, combined with the high power input requirement per unit of oxygen transferred, and the high incidence of microbial contamination in gas sparged systems have a substantially adverse influence upon the economics of the conventional fermentation processes.

Further, the passage of large quantities of air through the fermentation liquors, accompanied by vigorous agitation, often produces large quantities of foam in the reaction vessel which severely limits the working volume of the vessel. The fermentation process can be rendered inoperable and microbially contaminated when the air flow exit lines become filled with foam.

Many chemical and mechanical devices have been proposed and developed to solve the foaming problem in industrial biosynthesis. Most existing methods are based on chemical or mechanical defoaming of an already developed foam. Chemical treatment currently used for defoaming typically involves silicones and other water-immiscible additives which substantially decrease the rate of oxygen transfer, thus interfering with the processes of aerobic biosynthesis. Mechanical defoamers which are sometimes used in fermentation processes require additional power supply and special fermentor design. In addition, their performance is not uniformly reliable and feasible, especially in large fermentation volumes.

The novel invention conceived in this disclosure circumvents both of the foregoing described deficiencies of conventional systems related to mass transfer and defoaming in biotechnology. This invention relates to a unique apparatus which facilitates the molecular transport between liquids and gases such as occurs, for example, in chemical reactors, bioreactors (fermentors), photobioreactors, natural or artificial ponds and facilities for cultivation of fish, of micro- and macro-flora and for waste treatment.

EMBODIMENT OF THE INVENTION

The purpose of this invention is to apply a novel concept to chemical and fermentation reactors for promoting liquid phase reactions which depend on molecular transport to or from a gas phase. The application of the concept of this invention is particularly useful in aerobic fermentation processes, whereby molecular transport of oxygen is facilitated and the formation of unwieldy amounts of foam is mitigated. Another benefit of this invention is the removal of gas from liquids including deodorization.

An apparatus embodying the novel concept of this invention exposes a liquid medium to a gas phase by the flow of said liquid over a rotating surface whereby the flow of the liquid is caused by centrifugal force. The rotating surface can have various designs and individual dimensions but most commonly it will be a truncated cone whose included angle with the bottom of the cone is designed to provide the required flow rate of the fermentation medium at the rotational speeds found most advantageous for oxygen transfer from the gaseous phase, thus promoting the growth of aerobic microorganisms. The resultant of three forces (centrifugal, gravitational and Coriolis) raises the liquid in a thin film toward the upper edge of the rotating surface, thus facilitating molecular transport between the liquid and gas phases.

As the liquid reaches the upper circumference of the rotating surface it is flung or collected from the lip of the cone and returned to the rection vessel, where it resides during flow back into the center of the rotating cone. The liquid circulation thus generated within the vessel provides the necessary mixing of the cells of the microorganism being produced in the nutrient medium. Gas bubbles, which under conventional circumstances cause extensive foaming, are of smaller-than-usual size in the rising film and are rapidly released by the centrifugal field from the liquid into the gaseous phase. Two simultaneous effects are achieved: a high rate of oxygen transfer and the prevention of foaming. Thus our invention substantially differs from earlier practice in that it prevents foaming instead of eliminating an already existing foam, and provides the mass transfer of gases to liquids far more efficiently than the agitation and convectional flow methods of the prior art.

The thin film liquid flow on the cone surface is usually laminar, and mass transfer between the gaseous and liquid phases occurs solely on the exposed flat liquid surface. This action differs substantially from that employed in traditional methods of gas-liquid mass transfer by generating gas bubbles and turbulent flow in the liquid which leads to foaming. The rotating surface may be either continuous or segmented, scored, curved, corrugated or meshed; however, the preferred embodiment is a smooth truncated cone, the small-diameter end of which is positioned below the liquid interface in the reaction vessel. The included half-angle of the cone is preferably between 30° and 75°, but for most applications an included angle of 45° will be near-optimum. The material of the cone may be metal, particularly stainless steel, or coated steel, plastic or plastic mesh.

The figures of this disclosure show typical embodiments of our invention starting with its essential part, the rotating cone. Its modifications for special applications in mass transfer and in foam control during biological processes are also described.

BRIEF DESCRIPTION OF THE DRAWINGS

FIGS. 1 through 8 and the following descriptions demonstrate some of the possible modifications of the basic invention whereby mass transfer and foam control by liquid flow over the surface of a rotating cone is achieved.

FIG. 1a. Basic apparatus for mass transfer and foam control by liquid flow over a inner surface of the rotating cone.

FIG. 1b. Cross section of the rotating cone having a horizontal step and a sharp edged flange at the top of the cone.

FIG. 2a. Apparatus for mass transfer and foam control by liquid flow over the surface of a rotating cone having a paring channel and paring tube.

FIG. 2b. Plan view of the tangential positioning of the paring tube on the top of the rotating cone.

FIG. 3. Apparatus for mass transfer and foam control by liquid flow over the surfaces of two attached rotating cones.

FIG. 4. Apparatus for mass transfer and foam control by liquid flow over the surfaces of two rotating cones, the lower of which having a paring channel and paring tube.

FIG. 6. Apparatus for mass transfer and foam control by liquid flow over the surfaces of rotating cones whose greater circumference ends alternately face up-and-downward.

FIG. 7. Apparatus for mass transfer and foam control by liquid flow over the surfaces of rotating cones attached coaxially to a common shaft in a vertical cascade arrangement, employing reservoir vessels.

FIG. 8. Apparatus for mass transfer and foam control by liquid flow over the surfaces of rotating cones attached coaxially to a common shaft in a vertical cascade, employing paring channels and paring tubes.

DETAILED DESCRIPTION OF PREFERRED EMBODIMENTS

Figures 5A, 5B:
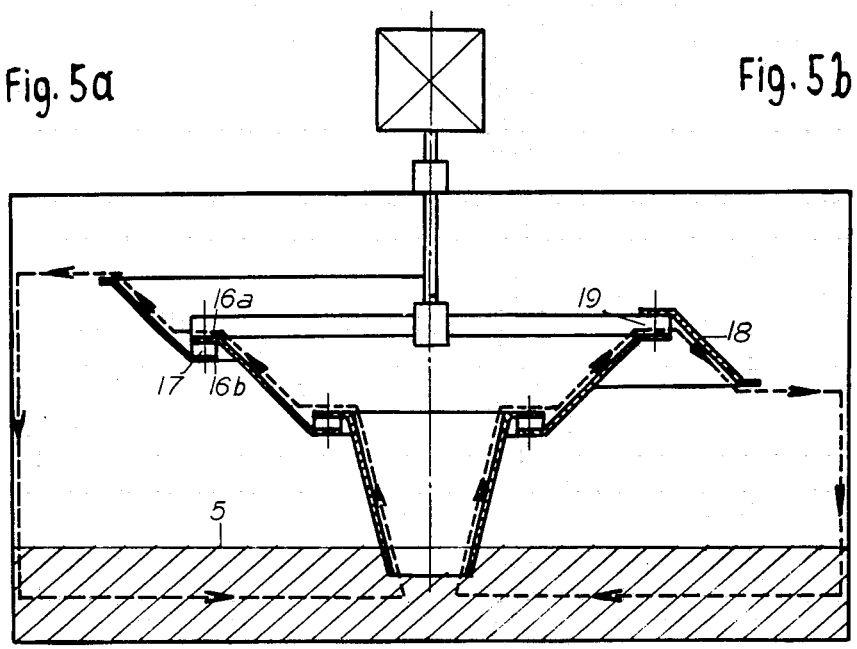
FIG. 5a. Left half of an apparatus for mass transfer and foam control by liquid flow over the surfaces of three concentric cones with their larger ends facing upward.
FIG. 5b. Right half of an apparatus for mass transfer and foam control by liquid flow over the surfaces of three concentric cones, the last one of which having its larger end facing downward.

FIG. 1a shows a simple frustrum of a cone (1) attached to a shaft (2) which rotates in a vessel (3) and is partly submerged at its small-diameter end in the liquid medium (5). The cone (1) has an open bottom (4) and an open top (6) which is reinforced by a flange (7). By centrifugal force the rotating cone (1) sucks liquid (5) from the open bottom (4) and creates a thin film (9) on the walls (10) of the cone (1) which film (9) is transported upward to the flange (7). Liquid is flung centrifugally from the edge of the flange (7) and drops hit the wall (11) of the vessel (3) and flow along the walls (11) into the original pool of liquid medium (5). The flow rate of liquid over the walls (10) of the cone frustrum (1) is controlled by the submergence depth of the open bottom, the included angle (4) into the pool of liquid medium (5), the included angle of the hollow cone (1), and by the rotational speed of the cone (1).

The liquid medium (5) which climbs due to centrifugal gravitational and Coriolis forces up the inner and outer surfaces of the cone (10) typically contains many gas bubbles. Centrifugal forces presses these bubbles toward the walls (10) of the cone (1) and the bubbles mechanically leave the liquid by moving toward the liquid-gas interphase where the bubbles are discharged to the gaseous phase. Even in every foamy substrates foaming is minimized by this action. Thus much higher aeration rates can be achieved while avoiding the need to add antifoam agents to the medium (5). Multiple stage mass transfer employing this action can be achieved. First, a thin rising film of liquid (9) is formed on the surface of the cone wall (10); then a liquid spray zone develops between the outer edge of the flange (7) and the wall (11) of the vessel (3). Finally, a thin liquid film forms on the wall (11) and flows into the liquid pool (5) covering the bottom of the cone (1).

FIG. 1b shows the same arrangement as in FIG. 1a except a horizontal step (12) at the wall of the cone is provided and the edge of the flange (8) at the top of the cone is beveled. The horizontal step (12) has two functions; first, it reinforces the rotating body of the cone (1), enhancing its stability during rotation especially at higher speeds. Second, mixing of the thin fluid layer and improved mass transfer occurs at the horizontal step (12) even if the film is very thin. The beveled edge of the flange (8) decreases the diameter of drops and thus enhances mass transfer between the gaseous and liquid phase.

FIGS. 2a and 2b show an arrangement where the discharging flange (8) at the top of the rotating cone is replaced by a paring channel (13) in which the liquid is collected and is then transported by paring tube (14) into vessel (3). The paring tube (14) provides more versatile transport of the liquid at the top of the rotating cones than does the flange. The paring tube (14) is stationary and is directed tangentially facing opposite to the direction of rotation of the cone thus collecting the liquid from the paring channel (13). In this way the tangential kinetic energy of the liquid is changed into hydrostatic energy. The liquid is pressured upward through the paring tube (14) then flows back into the vessel (3). Molecular mass transfer and foam control occur on the same cone surface between the thin liquid film and gaseous phase, as was the case for FIG. 1a.

FIG. 3. The same arrangement as in the FIG. 1 is shown in FIG. 3 except that the small-bottom diameter of the truncated cone (4) is attached to conical suction pipe (15) of smaller cone angle. The conical suction pipe (15) has a smaller half angle ($\alpha_1$) than the half angle ($\alpha_2$) of the larger, upper cone. This arrangement substantially enhances the area for mass transfer and enables suction of the medium from the open bottom (4) of the vessel (3). This arrangement also enhances uniform circulation of the total volume (5) of the vessel (3).

FIG. 4 shows a combination of the functions of the equipment described in FIGS. 1 and 2. A bottom cone of the type shown in FIG. 2 contains a paring channel (13) connected with paring tube (14) through which the pressurized liquid is transported into an upper cone whose function has been described in relation to FIGS. 1a and 1b. This cascade arrangement can be extended by adding axially more cones with paring channels and tubes.

FIG. 5 shows two different arrangements, indicated as 5a and 5b. An individual cone can be divided into several concentric surfaces, each of which has a flange on its inner edge (16b) and another flange on its outer edge (16a). By means of these flanges the cones can be assembled in a concentric multistage apparatus within which the effluent of the lower cone spatters on the wall of the adjacent upper cone. If an air gap (17) is left between the flanges connecting the cones a centrifugal fan effect is created increasing mass transfer to or from the turbulent gas phase above the thin liquid film flow. Foam also can be sucked from the vessel through the gap and broken on the wall of the rotating cone. The forced spattering of drops or liquid film from an inner cone of smaller diameter onto the outer cone of larger diameter enhances substantially the mixing in thin film. This action can also be used for deodorization, employing for example steam as the gasous phase.

The right side of the FIG. 5, (5b) differs from the left side (5a) in that the outermost cone (18) of the largest diameter is inverted. The inverted cone is ventilated by the ambient atmosphere drawn in at its top (19). This "multiple radial" arrangement has overflow and forced aeration of individual sections.

Figure 6:
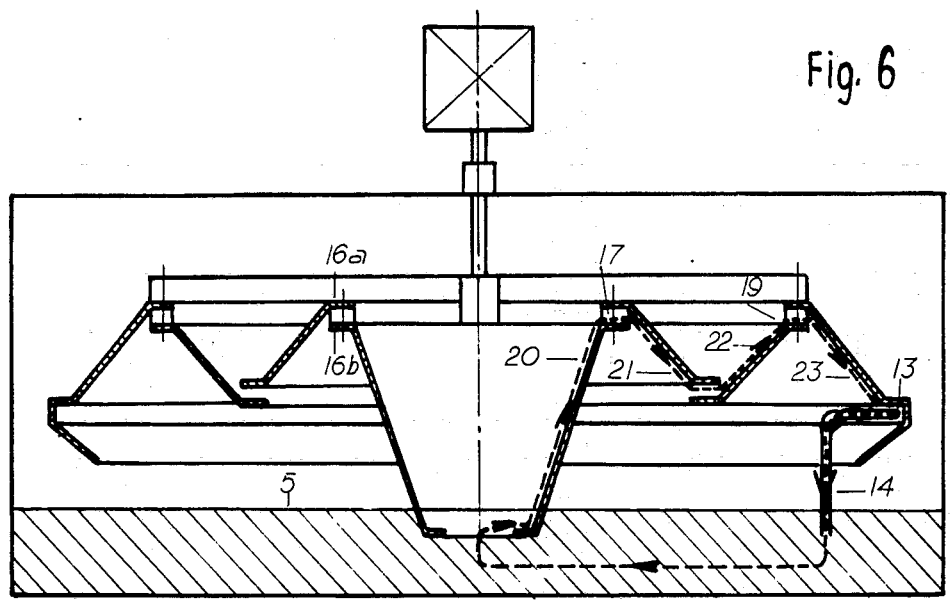

The arrangement in FIG. 6, having alternating downward and upward cone arrangement, has a constructional advantage when height of the fermentation or reaction vessel is a limiting factor. In the first inner stage (cone), centrifugal self-suction occurs from the liquid level of the vessel (5). The second stage cone (21) is inverted by its large end downward. The third and fourth stage cones (22) (23) are upright and inverted, respectively. In the fourth stage the cone is provided with a paring channel (13) from which the liquid is transported by a paring tube (14) below the level of the liquid in the vessel (3).

Figure 7:
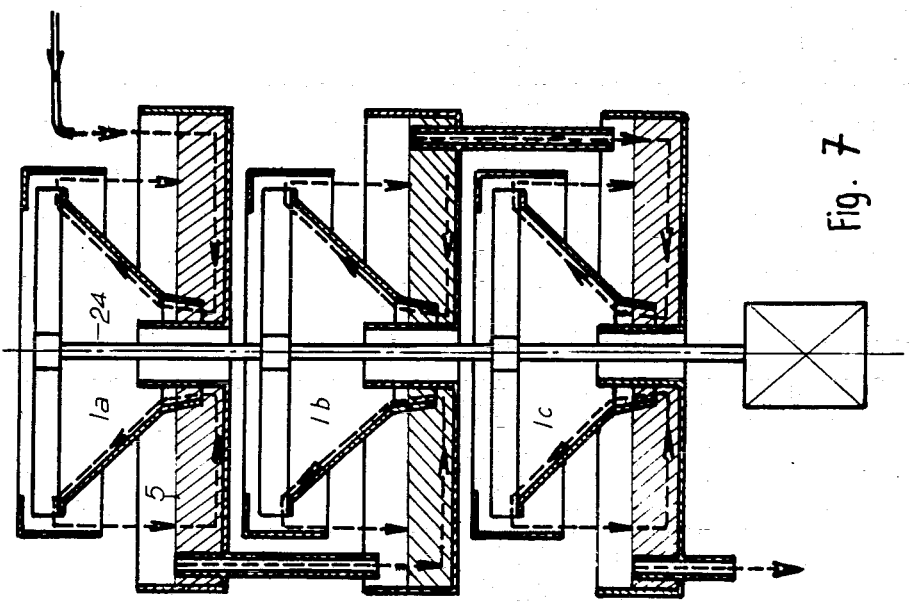

The principle of the arrangement in FIG. 7 is the same as in FIG. 1a, with the difference that cones (1) are attached coaxially on a common shaft (24). Sufficient distance between the cones (1) is provided to achieve the necessary air supply at the gas-liquid interface of each cone (1). Each rotating cone (1) independently sucks liquid from and recirculates it to the common pool (5).

Figure 8:
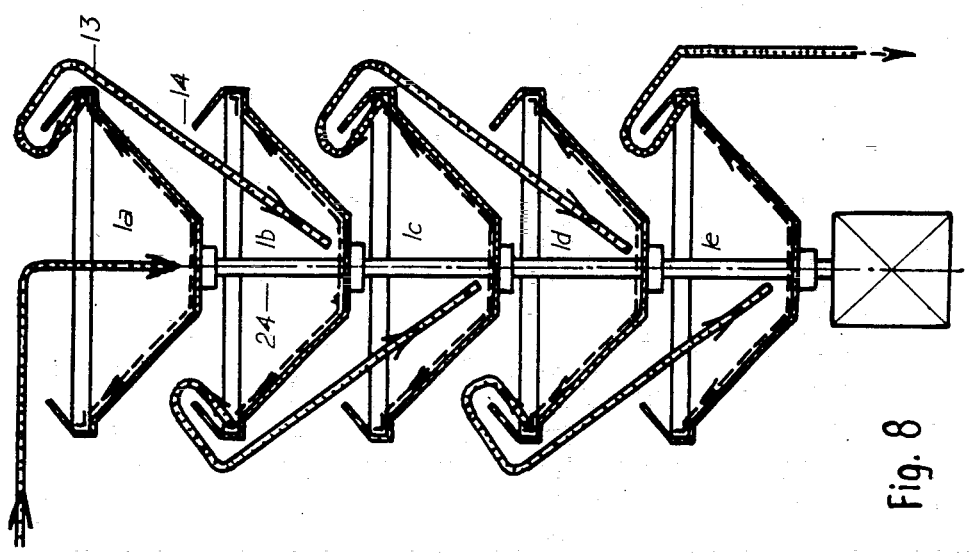

FIG. 8 shows a through-flow cascade of rotating cones (1a-1e) without interstage retention or retention vessel. Cones (1a-1e) are attached to a common shaft (24) and transport of the liquid between cones (1a-1e) is carried out by means of paring channels (13) and paring tubes (14). Liquid is fed into the center of the highest positioned cone (1a). Effluent is collected in a paring channel (13) and transported by a paring tube (16) into the center of the lower cone (1b). From the lowest cone (1e) the liquid is discharged by the system paring channel (13) and paring tube (14). This arrangement is advantageous for continuous process and deodorization or degasing of chemical and food products.

Figure 9:
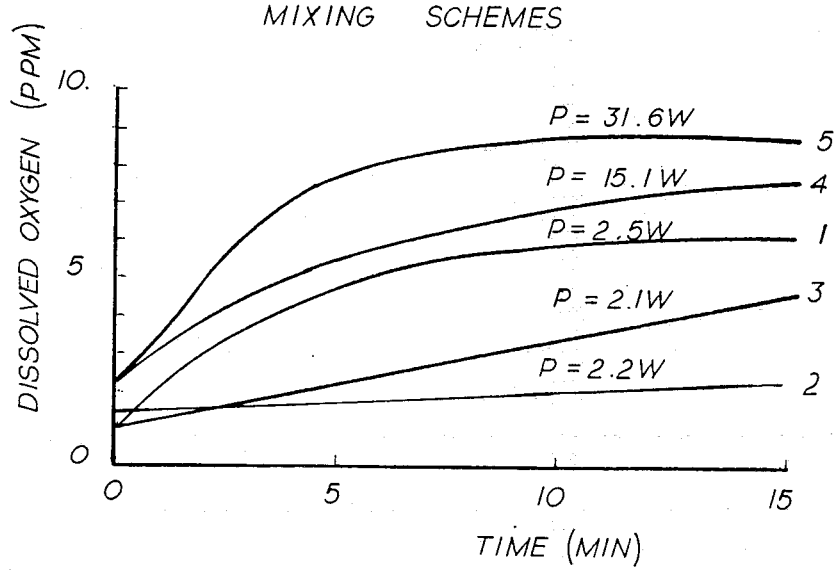
FIG. 9. Dissolved oxygen versus time curves for different oxygen transfer systems.

FIG. 9 shows graphically oxygen transfer rates for a traditional mixing system using an open turbine (curves 2 and 3) in comparison with oxygen transfer obtained by using thin film created by centrifugal force on the surface of frustrum of a cone (curves 1, 4 and 5). Power needed to carry out the particular oxygen transfer is given in watts.

EXAMPLES

Example 1

An open vessel containing 16 liters of water and employing the arrangement shown in FIG. 1a was used. At the start of the experiment, the water in the reaction vessel was stripped of oxygen by sparging with pure nitrogen. After all oxygen was stripped from the water a rotation of the cone submerged one inch under the surface was carried out at different speeds of rotations (150, 250 and 350 rpm).

Oxygen transport to and from the liquid phase was measured electrometrically by an oxygen-sensitive electrode. The results of this experiment for different rotation speeds are shown in FIG. 9 (curves 1, 4 and 5).

Example 2

The same arrangement as in example 1 was employed, except the cone was replaced by open propeller turbine rotating at 150 rpm, with and without air supply (one liter per minute) through a sparger beneath the turbine. FIG. 9 curves 2 and 3 shows the amount of oxygen transport under described conditions.

Example 3

In this experiment the apparatus was the same as described in Example 2, except that six grams of liquid dishwashing detergent (Janet Lee) were added to 16 liters of water. Air was then sparged beneath the turbine propeller at a rate of 100 cc per minute while the turbine impeller rotated at 150 rpm, which was found to be a sufficient speed to achieve a good molecular transport and significant mixing of the liquid contents in the reaction vessel. After two minutes the content of the reaction vessel was filled with foam. The turbine impeller was then turned off, removed from the reaction vessel, and replaced with the rotating cone described in Example 1a. The bottom of the cone was placed one inch below the static liquid-gas interface. The cone rotated at the same rate (150 rpm) used with the turbine impeller, and air was sparged below the cone in the same manner as when the turbine impeller was used. Under these conditions the foam in the vapor space above the liquid immediately began to disperse, and after three minutes the foam had nearly disappeared. This experiment illustrated the effectiveness of the rotating cone for both preventing foam formation and for the breaking of the already existing foam.

The foregoing examples show both the advantages of the rotating cone in promoting molecular transport to or from the liquid phase in a heterogeneous chemical reactor and the superiority of the rotating cone in foam control thus obviating the need for antifoam agents commonly used in fermentation processes.

We claim:

1. Equipment for improved mass transfer between gaseous and liquid phases, and for control of foaming, comprising:
a truncated conical mass transfer surface, having a greatest and a least periphery, axially connected to rotation means through shaft means, liquid containment means, liquid transport means for transporting said liquid phase from said liquid containment means to said least periphery, and for returning said liquid phase from said greatest periphery to said liquid containment means.

2. The equipment according to claim 1, wherein said rotation means rotates said truncated conical mass transfer surface at rotational velocities in the range of 10 to 500 revolutions per minute.

3. The equipment according to claim 1, wherein said truncated concical mass transfer surface comprises a conical surface having a half-angle in the range of 30 degrees to 75 degrees.

4. The equipment according to claim 1, wherein said truncated conical mass transfer surface comprises at least one horizontal step lying between said greatest periphery and said least periphery.

5. The equipment according to claim 1, wherein said shaft means mounts said first truncated conical mass transfer surface so that said least periphery contacts the surface of said liquid phase contained within said liquid containment means.

6. The equipment according to claim 1, wherein said greatest periphery comprises a substantially horizontal beveled lip.

7. The equipment according to claim 1, wherein said liquid transport means comprises a paring channel and paring tube.

8. The equipment according to claim 1, wherein said truncated conical mass transfer surface comprises truncated sections of conical surfaces comprising different included angles.

9. The equipment of claim 1 wherein said least periphery of said truncated conical mass transfer surface comprises a closed surface.

10. Equipment for improved mass transfer between gaseous and liquid phases, and for control of foam comprising:
a plurality of truncated conical mass transfer surfaces having greatest and least peripheries, spaced apart, and coaxially connected to rotation means through shaft means, liquid containment means, liquid transport means for transporting said liquid phase form said liquid containment means to and from successive truncated conical mass transfer surfaces, and from the last truncated conical mass transfer surface to said liquid containment means.

11. The equipment of claim 10 wherein each truncated conical mass transfer surface is connected to said shaft means with its greatest periphery above its least periphery.

12. The equipment of claim 10 wherein each truncated conical mass transfer surface is mounted to said shaft means with its greatest and least peripheries inverted with respect to the greatest and least peripheries of the next previous and next following truncated conical mass transfer surfaces.

13. The equipment of claim 10, wherein said rotation means rotates said truncated conical transfer surfaces at a rotational velocity in the range of 10 to 500 revolutions per minute.

14. The equipment of claim 10, wherein said greatest and least peripheries comprise a substantially horizontal lip.

15. The equipment of claim 10 wherein a first truncated conical mass transfer surface is connected to said shaft means with its greatest periphery above its lease periphery, a second truncated conical mass transfer surface connected to said shaft means positioned above said first truncated conical mass transfer surface with its greatest periphery position above its least periphery and wherein successive truncated conical mass transfer surfaces are connected to said shaft means with greatest and least peripheries inverted with respect to the greatest and least peripheries of the next previous and next following truncated conical mass transfer surfaces.

16. The equipment of claim 10 wherein said least peripheries of said truncated conical mass transfer surfaces comprise closed surfaces.

* * * * *

UNITED STATES PATENT AND TRADEMARK OFFICE
CERTIFICATE OF CORRECTION

PATENT NO. : 4,657,677

DATED : April 14, 1987

INVENTOR(S) : Roubicek, et al

It is certified that error appears in the above-identified patent and that said Letters Patent is hereby corrected as shown below:

On the title page, Item [19], "Roubickek et al." should read --Roubicek et al--

Item [54] should read --EQUIPMENT FOR ENHANCED MASS TRANSFER AND CONTROL OF FOAMING IN CHEMICAL AND BIOCHEMICAL PROCESSES--.

Item [57] line 13, "forming" should read --foaming--.

Column 5, line 39, "gasous" should read --gaseous--.

Signed and Sealed this

Eleventh Day of August, 1987

Attest:

DONALD J. QUIGG

*Attesting Officer*  *Commissioner of Patents and Trademarks*